United States Patent
Metcalf et al.

(10) Patent No.: US 7,636,639 B2
(45) Date of Patent: *Dec. 22, 2009

(54) FLUID MOTION AND COMPOSITION ANALYSIS DEVICE AND METHOD

(75) Inventors: Michael A. Metcalf, San Diego, CA (US); John M. Land, Godalming (GB)

(73) Assignee: Teledyne Isco, Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/580,308

(22) PCT Filed: Nov. 23, 2004

(86) PCT No.: PCT/US2004/039637

§ 371 (c)(1),
(2), (4) Date: Apr. 9, 2007

(87) PCT Pub. No.: WO2005/052547

PCT Pub. Date: Jun. 9, 2005

(65) Prior Publication Data

US 2007/0282539 A1 Dec. 6, 2007

(51) Int. Cl.
G01F 1/00 (2006.01)

(52) U.S. Cl. ....................................................... 702/45

(58) Field of Classification Search ................ 702/25, 702/29, 45, 48, 50, 54, 100, 103, 159; 73/861.18, 73/861.21, 861.25, 861.26
See application file for complete search history.

(56) References Cited

U.S. PATENT DOCUMENTS 5,483,499 A * 1/1996 Brumley et al. ............... 367/89
6,262,942 B1 * 7/2001 Stanton ........................ 367/90
6,487,916 B1 12/2002 Gomm et al.
6,983,208 B2 * 1/2006 Metcalf et al. ................ 702/45

* cited by examiner

*Primary Examiner*—Edward Raymond
*Assistant Examiner*—Mohamed Charioui
(74) *Attorney, Agent, or Firm*—Charmasson, Buchaca & Leach, LLP

(57) ABSTRACT

A remote sensor and associated data processor, performs concurrent analysis of backscattered signals from a multi-beam (6-10) acoustic Doppler emitter/receiver (1) positioned against the inside wall of a conveying pipe (2) or channel. Range-gating of the return signals allows independent analysis of discrete volumes of backscattered signal data corresponding to the distribution, concentration and travel velocity of small individual volumes or bins of water and suspended solids (4). Velocity is derived from the measured Doppler frequency shift for each bin. Relative solids concentration is estimated as a function of the measured intensity of the backscattered signals. The intensity data are calibrated by inputting site-specific environmental information, such as temperature, salinity, acoustical system constant, backscattered signal interpretation ratio between concentration and particle size, and concurrently measured concentration values obtained from physical sample collection and previous laboratory analysis into the analytical computer program. The program uses redundant iterative routines that adjust calibration parameters using data obtained from the previous measurement on an adjacent layer in a continuous self-correcting process. The apparatus and method provide both historical and real-time measurements of distribution, concentration and velocity of suspended solids in a flow of piped or channeled liquid (3).

41 Claims, 5 Drawing Sheets

US 7,636,639 B2

FLUID MOTION AND COMPOSITION ANALYSIS DEVICE AND METHOD

FIELD OF THE INVENTION

This invention relates to measurement of water quality, and more specifically to instruments used for measuring the concentration of suspended solids in a liquid flowing through a conduit.

BACKGROUND OF THE INVENTION

The safe disposal of sewer effluents and water treatment requires measurements of suspended solid concentration in treatment pipes, culverts and other conduits.

A sewer effluent containing a low value of suspended solid may be subject to a reduced treatment or no treatment at all. A plant treating sewer effluents from several municipalities may bill those municipalities in accordance with the volume flow and the total suspended solid concentration measured on the intake conduits from each municipality.

In the past, intrusive periodical samplings of solid-carrying water were taken and analyzed in laboratories to provide needed information about the solid contents of the water.

Various methods have been proposed to electronically measure total solid concentration in a volume of liquid, but no instrumentation has been provided for concurrently measuring suspended solid concentration as well as flow on a continuous, real time base.

This invention results from an attempt to provide a more practical instrumentation for use in sewer and water treatment plants.

SUMMARY OF THE INVENTION

The principal and secondary objects of this invention are to provide a non-intrusive method and apparatus for continuously measuring the total solid concentration in a liquid flowing through a pipe as well as the speed of various layers of flow within that pipe.

This and other valuable objects are achieved by placing an acoustical transmitter on the inside wall of a pipe or other conduit. The transmitter emits two pairs of obliquely divergent beams, one beam of each pair is aimed downstream from the other one in the pair. Echo signals of the emitted waveform are chopped into samplings corresponding to discrete volumes or pockets of the liquid in the pipe distributed along each beam. Doppler frequency shifts received from the beams are interpreted into velocity measurements of the solids within a number of flow layers within the pipe. The intensity of the backscattered echo signals are translated into solid concentration values using simplified algorithms combined with redundant iterative routines that adjust calibration parameters using data obtained from previous measurement on an adjacent layer in a continuous self-correcting process.

DESCRIPTION OF THE PREFERRED EMBODIMENT OF THE INVENTION

Figure 1:
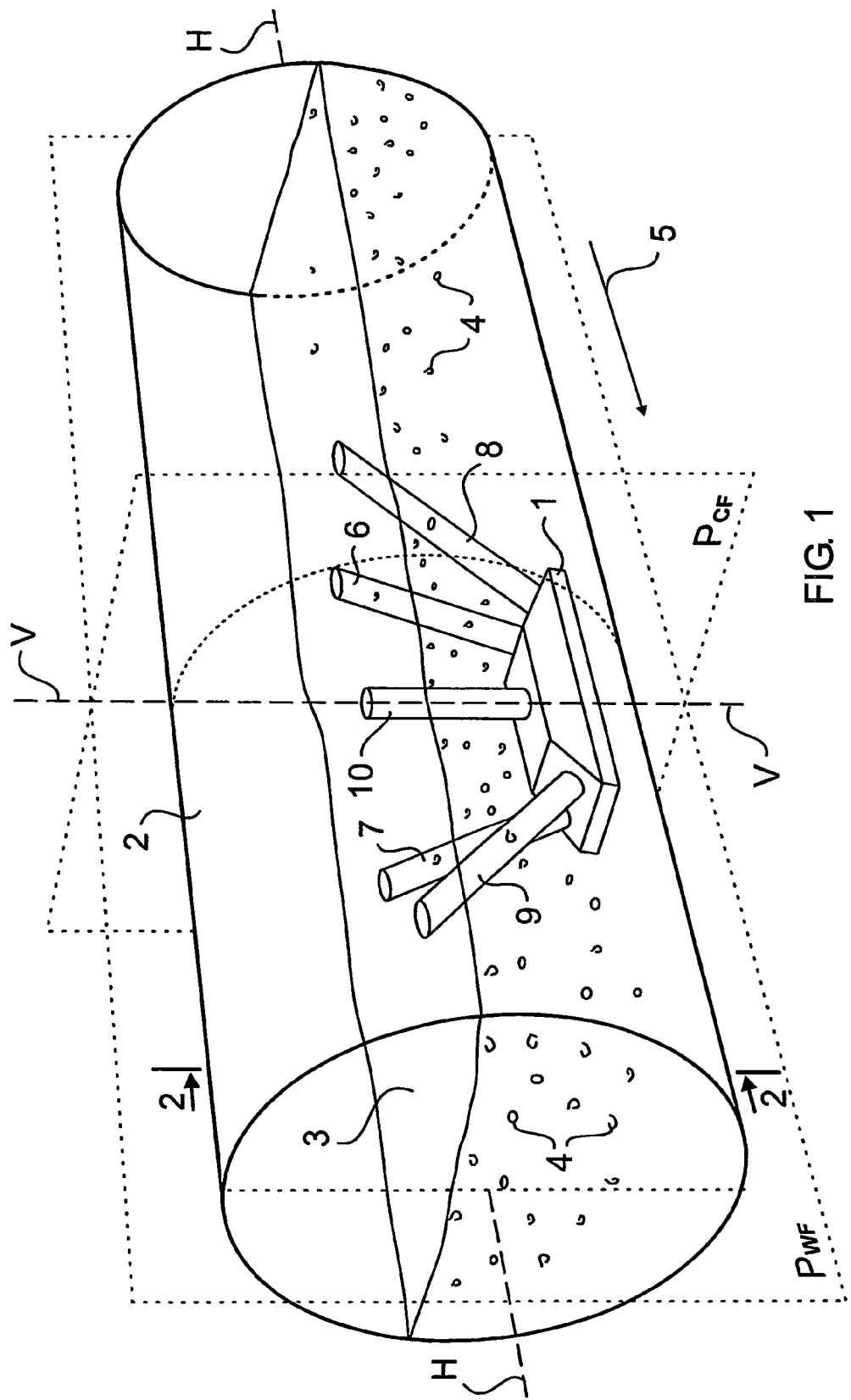
FIG. 1 is a diagrammatical perspective view of a conduit equipped with an flow and concentration transducer.
Figure 2:
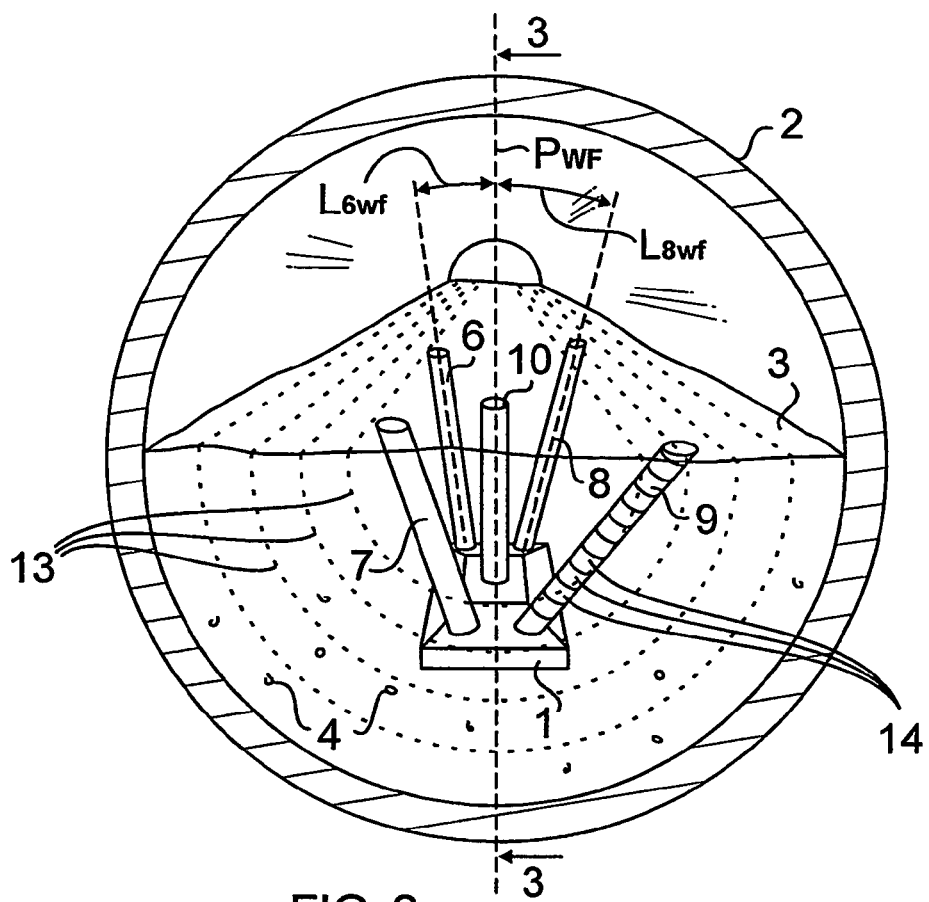
FIG. 2 is a diagrammatical cross-sectional end view thereof.
Figure 3:
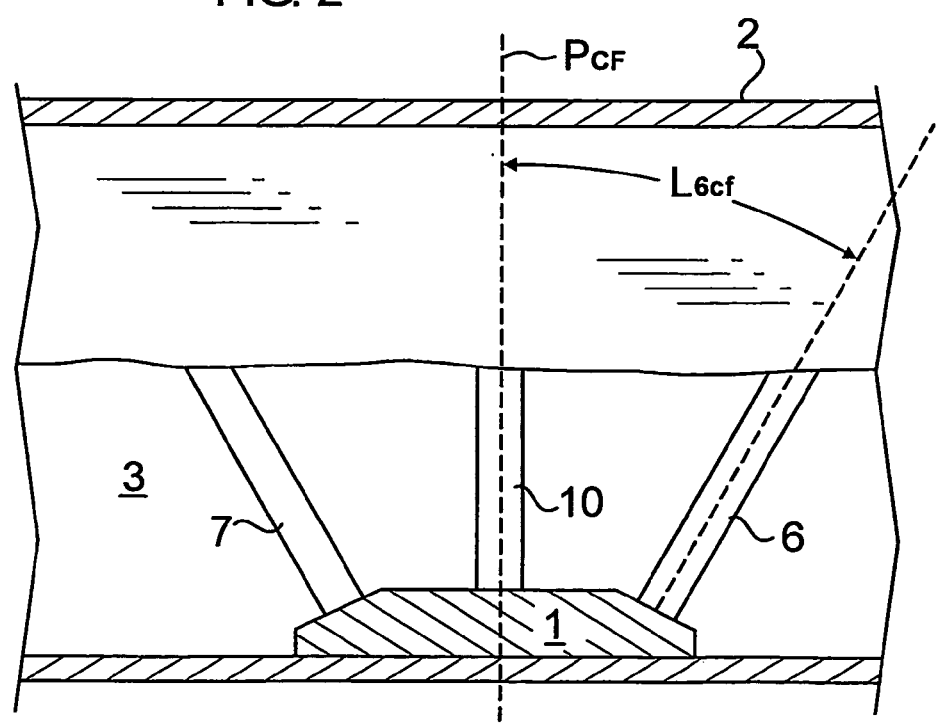
FIG. 3 is a diagrammatical cross-sectional side view thereof.
Figure 4:
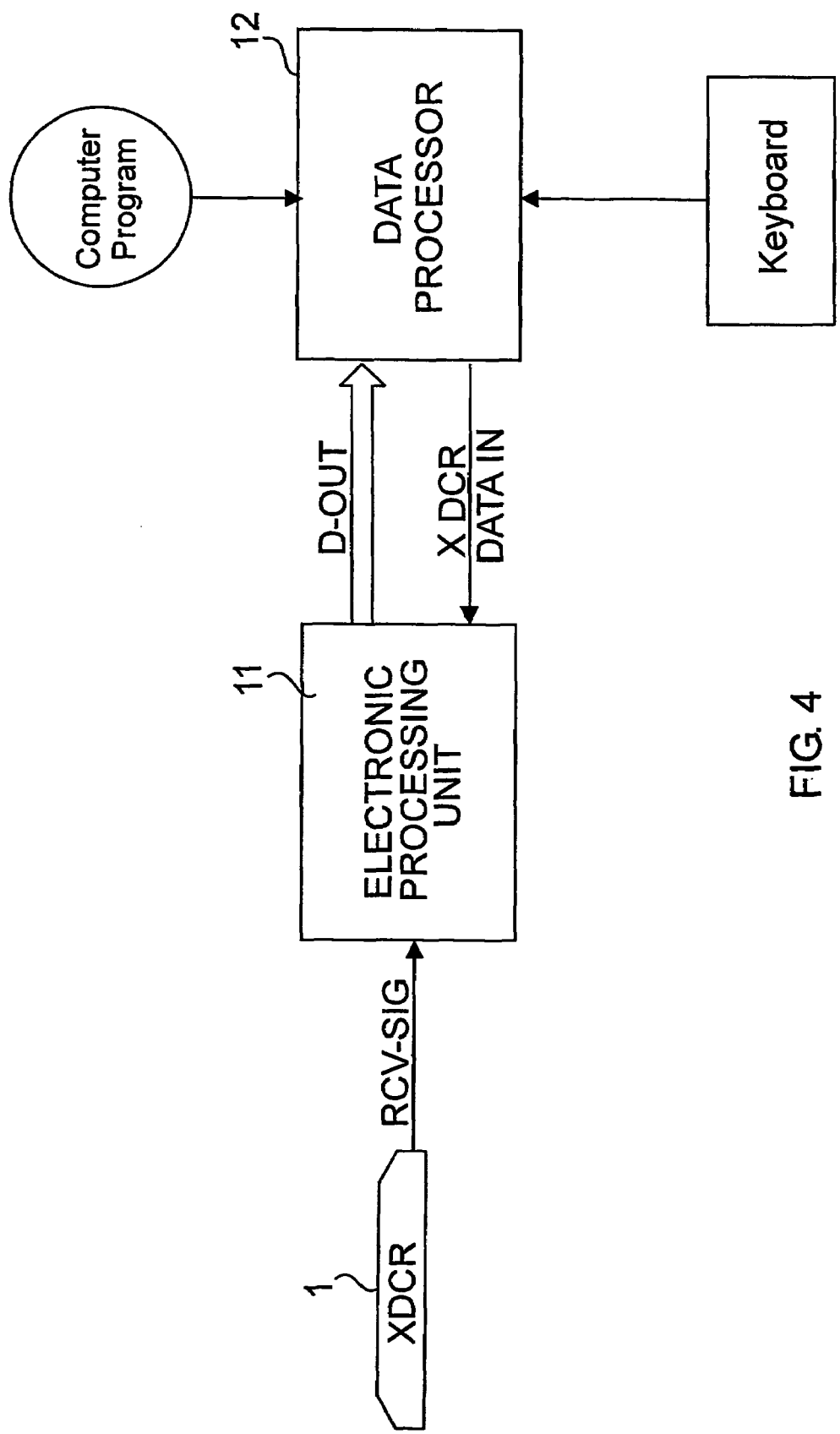
FIG. 4 is a block diagram of the concentration, distribution and flow velocity measurement instrument.
Figure 5:
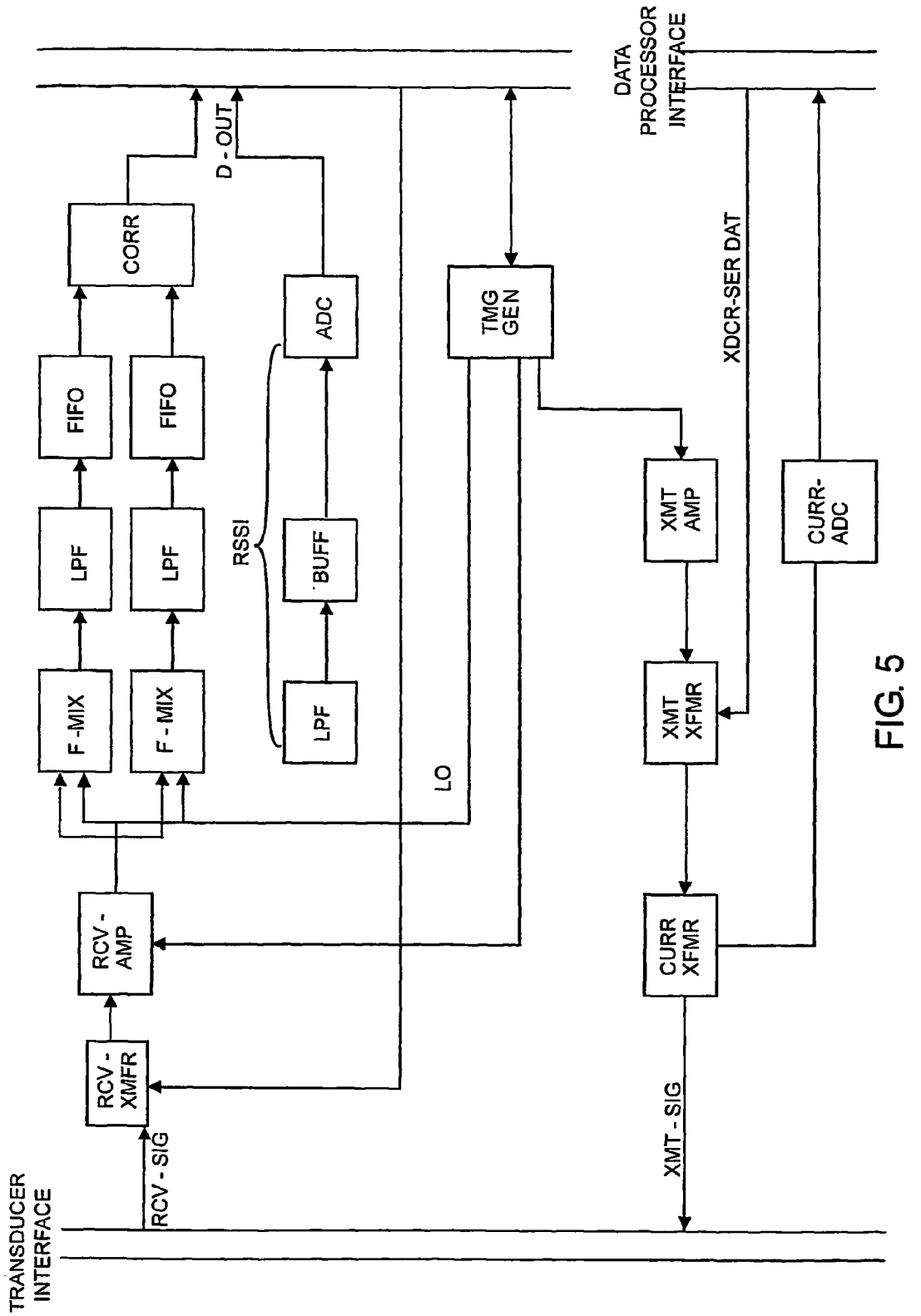
FIG. 5 is a block diagram of the electronic processing unit.

Referring now to the drawing, there is shown in FIGS. 1-3, a suspended solid velocity and concentration transducer 1 installed at the bottom of a pipe 2 carrying sewage water 3 containing suspended solids 4 and flowing in the direction indicated by the arrow 5 in FIG. 1. Piezoelectric ceramics in the transducer emit an acoustical waveform consisting of short pulses along four narrow beams 6, 7, 8, 9 pointing in different directions. The beams are grouped into two pairs in which a first beam 6, 8 is angled upstream at an angle $L_6$cf of about 20 degrees from the vertical, and the second beam 7, 9 in each pair is slanted downstream a the same angle as the first beam. As more specifically shown in FIG. 2, the planes of each pair of beams are aimed at a transversal angle $L_6$wf,$L_8$wf from the vertical and from the other pair of beams. Echo signals of the pulses are backscattered from the suspended solids 4. Since these solids have motion relative to the transducer, the echo signals are Doppler-shifted in frequency. A fifth ceramic transducer 10 mounted in the center of the transducer and aimed vertically is used to measure the depth of flow. As illustrated in FIGS. 4 and 5, the system includes an electronic processing unit 11 that receives an input signal RCVS-SIG from the transducer 1 and converts it into digital data D-OUT that is fed to a data processor 12. The system divides the echo signals into discrete regular intervals for samplings that correspond to different, discrete volumes of the flowing liquid. Velocity is calculated from the frequency shift measured in each sampling. The result is a profile of linear distribution of velocity along the beams illustrated by velocity profile lines 13 in FIG. 2. Each of the small divisions 14 shown along beam 9 of FIG. 2 represent an individual velocity measurement in a discrete volume known as a depth cell or bin. The velocity profile lines 13 are generated from velocity data measured by the upstream and downstream beam of each pair. The data from one beam pair are averaged to generate the profile lines.

Since Doppler measurements are directional, only the component of velocity along the direction of transmit and receive is measured. Narrow acoustic beams are used to accurately determine the horizontal velocity of the flow. The accuracy of the measurement is also enhanced by using gating times for the samplings that correspond to small volumes of approximately 5 centimeters in length and diameter. Potential bias in the return energy spectrum due to range dependent variables is avoided. The result is a very precise measurement of the vertical and transversal distribution of flow velocities. The velocity data from the two pairs of beams are entered into an algorithm to determine a mathematical description of the flow velocities throughout the entire cross-section of the liquid. The algorithm fits the basic functions of a parametric model to the actual data. The results predicts flow velocity at all points throughout the liquid. These results are integrated over the cross-sectional area to determine the discharge. The key benefit of this approach is that the system will operate accurately under different hydraulic conditions. As hydraulic conditions change, the change will manifest itself in the distribution of velocity throughout the depth of flow. As the system is measuring the velocity distribution directly, it will adapt to the changes in hydraulics, and generate a flow pattern that is representative of the new hydraulic conditions, insuring an accurate estimate of the flow rate. The measurement of distribution and concentration of the suspended solids 4 stem from a requirement of the frequency measurement circuits within the electronic processing unit 11 to receive a near-constant input voltage. An acoustic pulse emitted from the transducer 1 has a certain initial intensity that progressively diminishes as it travels through the liquid and is scattered from suspended particles. The reflected energy detected by the transducer is a very small fraction of that which was emitted. In addition, the return intensity of the backscattered vary considerably according to, but not limited to, the range to the point of energy reflection, the concentration of reflecting particles, and the water temperature. The received weakened signal RCV-SIG passes through an amplifier RCV-AMP that brings it to the level required by the frequency measurement circuits. A large loss of signal strength requires a large degree of amplification. The degree of amplification which is required is thus a measure of the loss of signal strength and, inversely, a measure of the intensity of the backscatter. The amount of amplification required is provided by the Receive Signal Strength Indicator RSSI. It is this measurement which facilitates the estimation of suspended solid concentration in the water column. In other words, the intensity value of the backscattered signal is translated into concentration values of the suspended solids and the frequency shifts of the receive signal is interpreted as an indication of velocity of solids in the flow of liquid.

As shown in FIG. 5, the transducer output signal RCV-SIG is routed to a receive coupling transformer RCV-XFMR that provides isolation and impedance matching. The signal is further amplified and bandwidth limited by the high gain selective log amplifier RCV-AMP. The amplified receive signal is fed to a pair of frequency mixers FMIX, where the signal is mixed replicatively with the local oscillator signal frequency LO. The desired base band signal, which is the difference frequency of the receive signal and the local oscillator frequency, is obtained by passing the mixer output signals through a pair of low pass filters LPF. The base band signals contain now the entire Doppler spectrum without the carrier signal. The mixers, are quadrature mixers, where an in-phase and a quadrature signal are obtained. Both signals are needed for the correlator CORR, which performs the basic digital signal processing. The in-phase and quadrature signals are buffered by a pair of first-in/first-out buffers FIFO and become part of the data D-OUT output to the data processor 12. The echo signals are also fed to a low-pass filter RSSI-LPF, then to a buffer RSSI-BUFF and digitized by an analog-to-digital converter RSSI-ADC. Finally, they are fed to the data processor as part of the output signal D-OUT.

A timing generator TMG-GEN generates all signals needed for the transmitter and receiver, such as the transmit signals, transmit enable, and the local oscillator quadrature signal for the mixer. The frequency of the pulses emitted by the transducer is 1.2288 MHz. A transmitter amplifier XMT-AMP acts as a power driver which buffers the logic level signal generated by the timing generator, and drives a transmitter output transformer XMT-XFMR, the transmit transformer also provides isolation between the electronic processing unit and the transducer.

The transmit current is monitored by a current transformer CURR-XFMR. Its output signal is scaled and digitized by an analog-to-digital converter CURR-ADC and is used as part of a built-in self-test by the data processor. All timing generator setups are fully programmable, and are down-loaded by the data processor to the timing generator's on an internal RAM.

The data processor is able to read back, the timing setup data and the digitized current sensed data.

Figure 6:
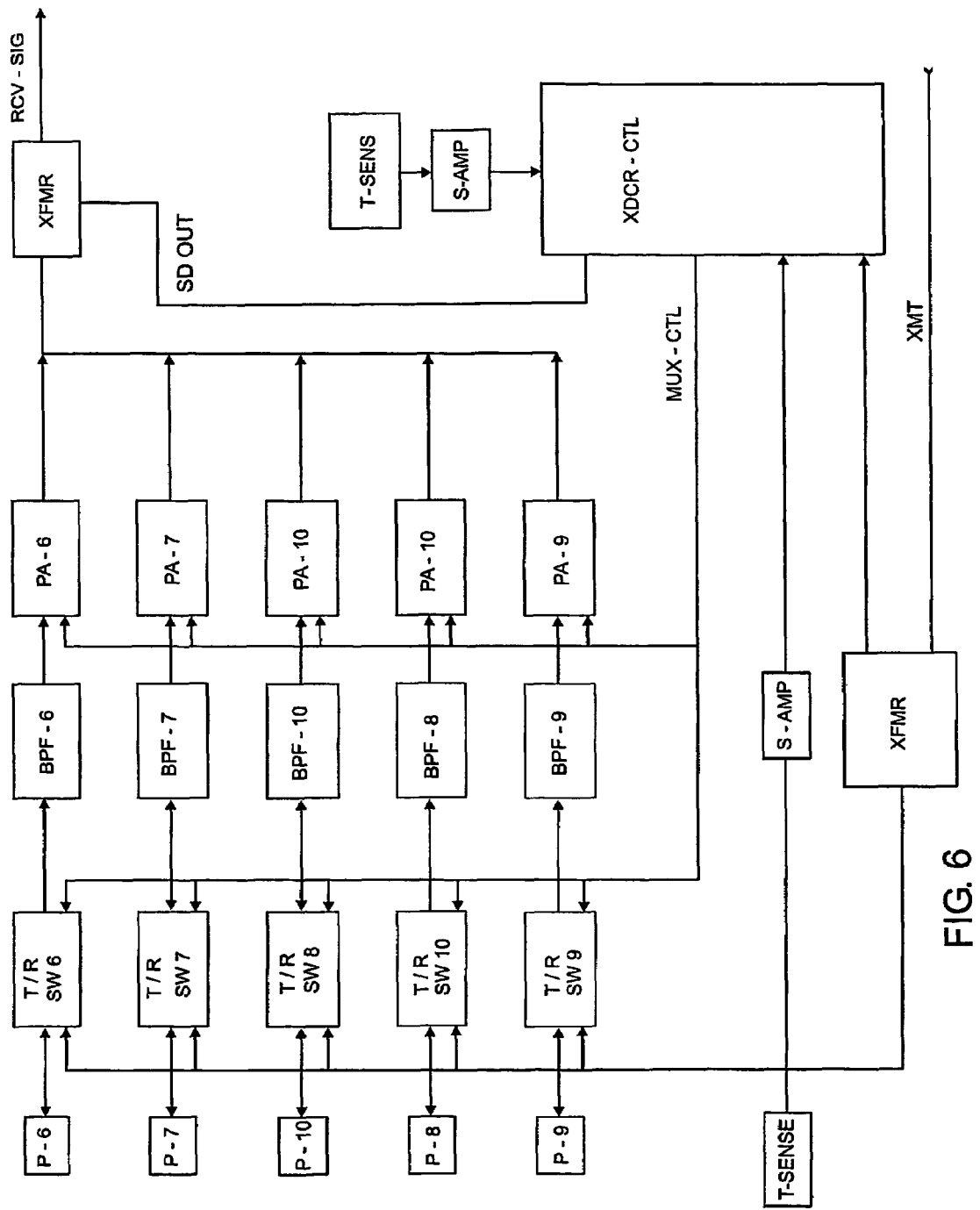
FIG. 6 is a block diagram of the transducer circuitry.

The transducer illustrated in FIG. 6 includes a signal transmit and receive multiplexer controlled by the electronic processing unit. The transmit signal generated by the timing generator TMG-GEN of the electronic processing unit passes through a coupling transformer XFMR which provides isolation and impedance matching. The signal is then multiplexed to one of the five beams by a selectable transmit/receive switch TJR-SW6-TJR-SW10. At the end of the transmitting phase, the multiplexer is deselected. As the echo signal is received from the Piezoelectric ceramics P-6 through P-10, it passes through the switch and one of the selected band pass filters BPF-6 through BPF-10 then to a preamplifier PA-6 through PA-10 and is converted to a differential signal by a wide band signal transformer XFMR before being fed to the electronic control unit. A thermistor T-SENSE is used to measure the transducer's ambient temperature. The temperature signal is scaled and buffered by an amplifier S-AMP, digitized by the transducer control XDCR-CTL and fed to the electronic control unit.

The following simplified formula of the acoustic theory governing backscatter from particles suspended in the water column identifies the main factors that contribute to the determination of suspended solids concentration from the intensity data.

$$E = SL + SV = \text{Constant} - 20\log(R) - 2\alpha_w R \quad \text{(Equation 1)}$$

where:

E=echo intensity,

SL=transmitted power,

SV=backscatter intensity due to the particles suspended in the water column, $\alpha_w$=a coefficient describing the absorption of energy by the water, R=the distance from the transducer to the measurement bin.

The echo intensity E measured by the system is a relative intensity, coming from direct measurement of the pressure amplitude of the return signal. Although the system will clearly recognize variations of echo intensity, it cannot determine the exact amount of backscatter intensity that is due solely to the presence of solids. Other factors that contribute to the final intensity must be removed.

The term 20 log(R) is a simple geometric function to account for the spherical spreading of the beam. This term can be further refined to include a near-field correction to the assumption of spherical spreading. Accurate knowledge of the velocity of sound is essential for determination of the range to a given measurement bin. The system computes a range based on the measured time and a sound velocity. Sound velocity is computed by using a user-defined salinity (assumed to be 0 for the sewer environment) and the temperature measured at the sensor head. This speed of sound is assumed by the method described here to be constant throughout the water column. This is a safe assumption in sewer environments as the depth of the flow is limited and the flow is well mixed.

It is not possible to make direct comparisons between the measurements made by different instruments unless the instruments have been calibrated in the field or the laboratory to establish their performance characteristics. The terms SL and Constant account for these differences and also deal with the characteristics of the suspended load. Understanding the manner in which instrument performance characteristics affect the data and correcting for these differences through field calibrations is key to the measurement method. This method makes use of the measured relative backscattered intensities and uses site-specific calibrations to compensate for such variations and determine a concentration of suspended solids.

The final two terms $\alpha_w$, and SV, refer to the absorption of acoustic energy by the water and the relative backscatter intensity. Acoustic energy is absorbed by water as it passes through it, and $\alpha_w$, is a measure of the amount of energy lost in this process. SV is the term we are interested in—the amount of energy that is backscattered by the presence of solids in the water column. An increase or decrease in the amount of solids will affect the value of SV. An additional term not included in Equation 1 must also be accounted for. This term describes the attenuation of the acoustic signal due to scattering and absorption by the suspended load.

To actually derive the mass concentration of total suspended solids TSS in the water from the measured intensity, one must determine the true backscattered sound intensity due to the presence of the solids. It can be shown that the relationship between the two parameters is as follows:

$$M(r) = (K <P_{rms}> r)^2 \frac{<a_s> \rho_s}{<f>^2} e^{4r(a_w+a_s)} \quad \text{(Equation 2)}$$

where:
M(r)=echo intensity,
K=transmitted power,
$P_{rms}$=backscatter intensity due to the particles suspended in the water column,
$\alpha_s$=particle radius
$\rho_s$=particle density
$\alpha_w$=a coefficient describing the absorption of energy by the water,
$\alpha_s$=a coefficient describing the absorption of energy by the water.

In this equation, the expected mass concentration, M(r) is a function of the sediment attenuation coefficient $\alpha_s$, which defines how the presence of solids attenuates the return signal. Both of these parameters are unknown. To provide a solution to this, it is necessary to use a numerical method. Computation of the mass concentration is performed without using a value of $\alpha_s$. The resulting value of M(r) is used to compute a value for $\alpha_s$. This computation process is iterated in the bin nearest to the sensor to derive final values of both sediment attenuation and mass concentration. This method is then applied in a step-wise manner along the successive bins of the profile.

The method proposed here to allow for the measurement of solids concentration on site, accomplishes this by using a simplified version of the above-expression:

$$\text{Log}_{10}M(r) = K_s + S[dB + 2r(\alpha_w + \alpha_s)] \quad \text{(Equation 3)}$$

dB is now the measured relative backscatter intensity, corrected for spherical spreading and any applicable near field effects. S is the relative backscatter coefficient that defines the relationship between solids concentration and particle size. $K_s$ is the site and instrument constant that corrects for the individual characteristics of a specific instrument at a given site. The other terms are as in Equation 2 and represent intensity attenuation by the presence of solids ($\alpha_s$) and water absorption ($\alpha_w$).

The amount of sound energy which is lost, or attenuated, due to the absorption by water has been found to depend on the frequency of the sound waves (i.e., of the instrument), and the salinity and the temperature of the water as follows:

$$\alpha_w = \frac{f}{91500}\left[\frac{1.86Sf_T f}{(f_T^2 + f^2)} + \frac{2.86 f}{f_T}\right] \quad \text{(Equation 4)}$$

where:
$\alpha_w$=the water absorption coefficient in Nepers/m
f=the instrument frequency, in MHz
S=the salinity in ppt.

The term, $f_T$, is called the Relaxation Frequency and is given by the following expression:

$$f_T = 21.9 \times 10^{(6-\frac{1520}{273+T})} \quad \text{(Equation 5)}$$

where: T is the water temperature in degrees Celsius.

Using these formulae, the attenuation of the signal due to water absorption, per meter, may be computed and hence, using the slant length of the bin, the total attenuation of sound through each measurement interval, or "bin", can be derived.

When sound passing through the water column strikes particles of suspended solids, the energy is attenuated both by scattering and absorption by the solid media. The degree of scattering depends on the relationship between the frequency and the size of the particle. Frequency may be expressed in terms of the Wave Number, k, where:

$$k = \frac{2\pi f}{V_s} \quad \text{(Equation 6)}$$

where:
f=the instrument frequency in Hertz
$V_s$=the salinity in ppt.

When the value of the product $k\alpha_s$ (where $\alpha_s$ is the particle radius) is well below 0.5, Rayleigh scattering occurs. This is the range normally found during suspended sediment measuring conditions. The sediment constant, $\zeta_1$, is given by:

$$\zeta_1 = \frac{K_\alpha}{\rho_s} k^4 a_s^3 \quad \text{(Equation 7)}$$

where:
$\rho_s$=the density of the sediment in kg/m³
$K_\alpha$=a term relating to compressibility and density (normal value 0.18)

The actual sediment attenuation per meter due to scattering, $\alpha_1$ (Nepers/m), by the solids in a region at range, r, and with a mass concentration of $M_r$ (kg/m³) is then given by:

$$\alpha_1 = M_r \times \zeta_1 \quad \text{(Equation 8)}$$

Acoustic energy is also absorbed by sediment in the water column. The following expression (Urick, 1948) is used to determine the sediment attenuation per meter due to this absorption, $\alpha_2$ (Nepers/m):

$$\alpha_2 = \frac{M_r k(\sigma-1)^2}{2\rho_s}\left[\frac{s}{s^2 + (\sigma+\delta)^2}\right] \quad \text{(Equation 9)}$$

where:

$$\sigma = \frac{\rho_s}{\rho_w}$$

$$s = \frac{9}{4\beta a_s}\left[1 + \frac{1}{\beta a_s}\right]$$

$$\beta = \left[\frac{kV_s}{2v_w}\right]^{\frac{1}{2}}$$

where:
$\rho_s$=the density of the solid particles
$\rho w$=the density of the water
$v_w$=the kinematic viscosity of the water.

The above-expressions are valid for values of the product $k\alpha_s$, being much less than unity. This is the region where attenuation due to scattering becomes negligible and viscous absorption begins to dominate.

The method combines the attenuation due to scattering and absorption into a single Sediment Attenuation Coneficient SAC. The SAC can either be defined by the user or can be computed by the processing software using a nominal, or "effective", particle size in combination with assumed values for particle specific gravity (2.7) and compressibility (0.18). In both cases, the input values are inevitably estimates and must be refined by iteration within the software's Calibration Module.

It is almost impossible, in practice, to calculate from first principles the sediment attenuation coefficient for a natural population of sediment. The approach used in the software is a pragmatic approach in which workable values of the coefficient are established using actual observational data. It therefore, becomes somewhat academic as to whether or not the input values of, for example, particle size and compressibility are correct.

The computer program CP controlling the data processor carries out all of the computations required to derive sediment concentrations from measured backscatter intensity, according to the simplified Equation 3 and a value for sediment attenuation derived by calibration. The program imports the backscatter data (expressed in instrument counts) and ancillary information (e.g., temperature, salinity, etc.) from raw system data files. The user may either input specific site calibrations values (e.g., values for S and Ks) on the keyboard or have the program determine these values from entered data. The user also input values for TSS that were measured by taking samples of water and having them analyzed by a laboratory for TSS values. These sample are taken concurrently with the system data so that a direct calibration between system-measured values and actual values can be determined.

The program then takes the raw measured data from the first valid measurement bin below each transducer. It calculates the various required parameters and solves Equation 3, using the iterative routine, to find the suspended sediment concentration in the first whole bin and in the interval between the transducers and the first bin (where the system cannot obtain data). The computed solids concentrations and sediment attenuation are then fed into the system again in order to make the relevant corrections in the next bin, which is then solved using a similar iterative process. The procedure is repeated until the last whole bin has been solved. The software then moves on to the next ensemble of data.

Following this, the program displays the calculated concentrations and compares them to the actual measured concentrations. Errors between the two data sets, calculated then actual, are also displayed as functions of depth and concentration. The user then adjusts the different parameters (S, Ks, and the SAC) to improve the correlation between data sets. As this is an iterative process, and some parameters are initially given seed values, the user adjusts the parameters to increase the correlation between the two data sets and reduce the errors to zero, while observing the results of their actions in real-time.

The method can be utilized in the sanitary sewer environment, and can provide both historical and real-time measurement of TSS in addition to flow measurement. This will allow users to measure total mass transport of solids within sanitary sewer systems as well as the volume transport of water. The method described here uses data from multiple beams to accomplish this. The method has the ability to look at the spatial distribution of solids concentration in the depth of flow as well as total solids concentration.

The invention claimed is:

1. An apparatus, for measuring concentration, distribution and velocity of solids suspended in a flowing liquid, which comprises:
a transmitter emitting at least one directional beam of an acoustical waveform;
at least one detector receiving echo signals of said waveform backscattered from said solids;
means for gathering measured intensity value of said echo signals;
means for measuring Doppler frequency shifts of said echo signals; and
data processing equipment comprising means for translating said intensity values into concentration values of said solids, and means for interpreting said frequency shifts into velocity measurements of said solids;
wherein said means for translating comprises means for calibrating said intensity values by inputting current site specific environmental information taken concurrently from said flowing liquid about said flowing liquid.

2. The apparatus of claim 1, wherein said flowing liquid is contained in a conduit having a directional flow, and said transmitter and detector are located inside said conduit.

3. The apparatus of claim 2, wherein said transmitter emits at least a first pair of said beams from substantially the same location, a second beam in said pair being aimed downstream from a first beam and at a longitudinal angle from said first beam.

4. The apparatus of claim 3 which further comprises a second of said pair of beams aimed at a transversal angle from said first pair of beams.

5. The apparatus of claim 4 which further comprises means for generating samplings of said echo signals corresponding to discrete volumes of said liquid distributed along said beams.

6. The apparatus of claim 5, wherein said means for translating comprises means for calibrating said intensity values by inputting site specific environmental information.

7. The apparatus of claim 6, wherein said wherein said data processing equipment further comprises program means for adjusting at least one calibration parameter in translating intensity value from one of said volumes using values obtained from another volume along the same beam.

8. The apparatus of claim 6, wherein said means for calibrating comprises means for automatically entering information, and means for manually entering information.

9. The apparatus of claim 5, wherein said means for translating comprise means for computing a mass concentration of solid M(r) per unit volume at a range r according to the formula:

$$\text{Log}_{10}M(r)=K_s+S[dB+2r(\alpha_w+\alpha_s)]$$

wherein $K_s$ is a site and instrument constant,

S is a relative backscattered coefficient defining the relationship between solid concentration and particle size, dB is the measured relative backscattered intensity, $\alpha_w$ is a water attenuation coefficient, and $\alpha_s$ is an attenuation coefficient due to the presence of solids.

10. The apparatus of claim 9, wherein said means for translating further comprise:

means for using M (r) values obtained in connection with one of said volumes to compute said attenuation coefficient $\alpha_s$; and means for inputting said $\alpha_s$ value in translating said intensity value into an M (r) value for the next of said volume farther away from said transmitter.

11. The apparatus of claim 5, wherein said means for translating further comprises means for entering concentration values obtained from a previous measurement.

12. The apparatus of claim 1 which further comprises means for generating samplings of said echo signals corresponding to discrete volumes of said liquid distributed along said beam and wherein said means for calibrating further comprises inputting site specific instrument constant information.

13. The apparatus of claim 12, wherein said means for translating comprise means for computing a mass concentration of solid M(r) per unit volume at a range r according to the formula:

$$\text{Log}_{10}M(r)=K_s+S[dB+2r(\alpha_w+\alpha_s)]$$

wherein $K_s$ is a site and instrument constant,

S is a relative backscattered coefficient defining the relationship between solid concentration and particle size, dB is the measured relative backscattered intensity, $\alpha_w$ is a water attenuation coefficient, and $\alpha_s$ is an attenuation coefficient due to the presence of solids.

14. The apparatus of claim 13, wherein said means for translating further comprise:

means for using M(r) values obtained in connection with one of said volumes to compute said attenuation coefficient $\alpha_s$; and, means for inputting said $\alpha_s$ value in translating said intensity value into an M(r) value for the next of said volume farther away from said transmitter.

15. The apparatus of claim 12, wherein said means for translating further comprises means for entering suspended solids concentration values obtained from a previous measurement.

16. The apparatus of claim 1, wherein said data processing equipment further comprises program means for adjusting at least one calibration parameter in translating intensity value from one of said volumes using values obtained from another volume along the same beam.

17. The apparatus of claim 1, wherein said means for calibrating comprises means for automatically entering information, and means for manually entering information.

18. A method for measuring concentration, distribution and velocity of solids suspended in a flowing liquid, which comprises:

emitting at least one directional beam of an acoustical waveform across said liquid;

detecting echo signals of said waveform backscattered from said solids;

gathering measured intensity value of said echo signals;

measuring Doppler frequency shifts of said echo signals;

translating said intensity values into concentration values of said solids; and interpreting said frequency shifts into velocity measurements of said solids;

wherein said translating comprises calibrating said intensity values by inputting current site specific environmental information taken concurrently from said flowing liquid about said flowing liquid.

19. The method of claim 18, wherein said flowing liquid is contained in a conduit having a directional flow, and said transmitter and detector are located inside said conduit.

20. The method of claim 19, wherein said emitting comprises transmitting at least a first pair of said beams from substantially the same location, a second beam in said pair being aimed downstream from a first beam and at a longitudinal angle from said first beam.

21. The method of claim 20 which further comprises emitting a second of said pair of beams aimed at a transversal angle from said first pair of beams.

22. The method of claim 21 which further comprises samplings of said echo signals corresponding to discrete volumes of said liquid distributed along said beams.

23. The method of claim 22, wherein said translating comprises calibrating said intensity values by inputting site specific environmental information.

24. The method of claim 23, wherein said data processing equipment further comprises program adjusting at least one calibration parameter in translating intensity value from one of said volumes using values obtained from another volume along the same beam.

25. The method of claim 23, wherein said calibrating comprises automatically entering information, and manually entering information.

26. The method of claim 22, wherein said translating comprise computing a mass concentration of solid M(r) per unit volume at a range r according to the formula:

$$\text{Log}_{10}M(r)=K_s+S[dB+2r(\alpha_w+\alpha_s)]$$

wherein $K_s$ is a site and instrument constant,

S is a relative backscattered coefficient defining the relationship between solid concentration and particle size, dB is the measured relative backscattered intensity, $\alpha_w$ is a water attenuation coefficient, and $\alpha_s$ is an attenuation coefficient due to the presence of solids.

27. The method of claim 26, wherein said translating further comprise:

using M (r) values obtained in connection with one of said volumes to compute said attenuation coefficient $\alpha_s$; and inputting said $\alpha_s$ value in translating said intensity value into an M(r) value for the next of said volume farther away from said transmitter.

28. The method of claim 22, wherein said translating further comprises entering concentration values obtained from a previous measurement.

29. The method of claim 20 which further comprises generating samplings of said echo signals corresponding to discrete volumes of said liquid distributed along said beam, and wherein said calibrating further comprises inputting site specific instrument constant information.

30. The method of claim 29, wherein said translating comprise computing a mass concentration of solid M(r) per unit volume at a range r according to the formula:

$$\text{Log}_{10}M(r)=K_s+S[dB+2r(\alpha_w+\alpha_s)]$$

wherein $K_s$ is a site and instrument constant,

S is a relative backscattered coefficient defining the relationship between solid concentration and particle size, dB is the measured relative backscattered intensity,
$\alpha_w$ is a water attenuation coefficient, and
$\alpha_s$ is an attenuation coefficient due to the presence of solids.

31. The method of claim 30, wherein said translating further comprise:
   using M(r) values obtained in connection with one of said volumes to compute said attenuation coefficient $\alpha_s$; and
   inputting said $\alpha_s$ value in translating said intensity value into an M(r) value for the next of said volume farther away from said transmitter.

32. The method of claim 29, wherein said translating further comprises entering suspended solids concentration values obtained from a previous measurement, and site specific instrument constant information.

33. The method of claim 18, which further comprises adjusting at least one calibration parameter in translating intensity value from one of said volumes using values obtained from another volume along the same beam.

34. The method of claim 18, wherein said calibrating comprises automatically entering information, and manually entering information.

35. The method of claim 18, wherein said information comprises water temperature.

36. The method of claim 18, wherein said information comprises water salinity.

37. An apparatus, for measuring concentration, distribution and velocity of solids suspended in a flowing liquid, which comprises:
   a transmitter emitting at least one directional beam of an acoustical waveform;
   at least one detector receiving echo signals of said waveform backscattered from said solids;
   means for gathering measured intensity value of said echo signals;
   means for measuring Doppler frequency shifts of said echo signals; and
   data processing equipment comprising means for translating said intensity values into concentration values of said solids, and means for interpreting said frequency shifts into velocity measurements of said solids;
   wherein said means for translating comprises means for calibrating said intensity values by inputting site specific environmental information;
   said apparatus which further comprises means for generating samplings of said echo signals corresponding to discrete volumes of said liquid distributed along said beam;
   wherein said means for translating further comprises means for entering suspended solids concentration values obtained from a previous measurement; and,
   wherein said site specific environmental information comprises water temperature, salinity and acoustical system constants, and echo signal assignment ratio between concentration and particle size.

38. An apparatus, for measuring concentration, distribution and velocity of solids suspended in a flowing liquid, which comprises:
   a transmitter emitting at least one directional beam of an acoustical waveform;
   at least one detector receiving echo signals of said waveform backscattered from said solids;
   means for gathering measured intensity value of said echo signals;
   means for measuring Doppler frequency shifts of said echo signals; and
   data processing equipment comprising means for translating said intensity values into concentration values of said solids, and means for interpreting said frequency shifts into velocity measurements of said solid;
   wherein said means for translating comprises means for calibrating said intensity values by inputting site specific environmental information;
   wherein said flowing liquid is contained in a conduit having a directional flow, and said transmitter and detector are located inside said conduit;
   wherein said transmitter emits at least a first pair of said beams from substantially the same location, a second beam in said pair being aimed downstream from a first beam and at a longitudinal angle from said first beam;
   wherein said apparatus further comprises a second of said pair of beams aimed at a transversal angle from said first pair of beams;
   wherein said apparatus further comprises means for generating samplings of said echo signals corresponding to discrete volumes of said liquid distributed along said beams;
   wherein said means for translating further comprises means for entering concentration values obtained from a previous measurement; and,
   wherein said site specific environmental information comprises water temperature, salinity and acoustical system constants, and echo signal assignment ratio between concentration and particle size.

39. A method for measuring concentration, distribution and velocity of solids suspended in a flowing liquid, which comprises:
   emitting at least one directional beam of an acoustical waveform across said liquid;
   detector receiving echo signals of said waveform backscattered from said solids;
   gathering measured intensity value of said echo signals;
   measuring Doppler frequency shifts of said echo signals;
   translating said intensity values into concentration values of said solids; and
   interpreting said frequency shifts into velocity measurements of said solids;
   wherein said translating comprises calibrating said intensity values by inputting site specific environmental information;
   which further comprises generating samplings of said echo signals corresponding to discrete volumes of said liquid distributed along said beam;
   wherein said translating further comprises entering suspended solids concentration values obtained from a previous measurement; and,
   wherein said site specific environmental information comprises water temperature, salinity and acoustical system constants, and echo signal assignment ratio between concentration and particle size.

40. A method for measuring concentration, distribution and velocity of solids suspended in a flowing liquid, which comprises:
   emitting at least one directional beam of an acoustical waveform across said liquid;
   detector receiving echo signals of said waveform backscattered from said solids;
   gathering measured intensity value of said echo signals;
   measuring Doppler frequency shifts of said echo signals;
   translating said intensity values into concentration values of said solids; and
   interpreting said frequency shifts into velocity measurements of said solids;

wherein said translating comprises calibrating said intensity values by inputting site specific environmental information;

wherein said flowing liquid is contained in a conduit having a directional flow, and said transmitter and detector are located inside said conduit;

wherein said emitting comprises transmitting at least a first pair of said beams from substantially the same location, a second beam in said pair being aimed downstream from a first beam and at a longitudinal angle from said first beam;

which further comprises emitting a second of said pair of beams aimed at a transversal angle from said first pair of beams;

which further comprises samplings of said echo signals corresponding to discrete volumes of said liquid distributed along said beams;

wherein said translating further comprises entering concentration values obtained from a previous measurement; and, wherein said site specific environmental information comprises water temperature, salinity and acoustical system constants, and echo signal assignment ratio between concentration and particle size.

41. A method for measuring concentration, distribution and velocity of solids suspended in a flowing liquid, which comprises;

emitting at least one directional beam of an acoustical waveform across said liquid;

detecting echo signals of said waveform backscattered from said solids;

gathering measured intensity value of said echo signals;

measuring Doppler frequency shifts of said echo signals;

translating said intensity values into concentration values of said solids; and interpreting said frequency shifts into velocity measurements of said solids;

wherein said translating comprises calibrating said intensity values by inputting current site specific environmental information about said flowing liquid;

wherein said information comprises echo signal assignment ratio between concentration and particle size.

* * * * *